US00PP28159P3

(12) United States Plant Patent
van Kleinwee

(10) Patent No.: US PP28,159 P3
(45) Date of Patent: Jul. 4, 2017

(54) *PETUNIA* PLANT NAMED 'PEHY0012'

(50) Latin Name: *Petunia hybrida*
Varietal Denomination: PEHY0012

(71) Applicant: SYNGENTA PARTICIPATIONS AG, Basel (CH)

(72) Inventor: Theodorus Cornelis van Kleinwee, Enkuizen (NL)

(73) Assignee: Syngenta Participations AG, Basel (CH)

( * ) Notice: Subject to any disclaimer, the term of this patent is extended or adjusted under 35 U.S.C. 154(b) by 12 days.

(21) Appl. No.: 14/757,335

(22) Filed: Dec. 17, 2015

(65) Prior Publication Data

US 2016/0198615 P1 Jul. 7, 2016

Related U.S. Application Data

(60) Provisional application No. 62/099,638, filed on Jan. 5, 2015.

(51) Int. Cl.
*A01H 5/02* (2006.01)

(52) U.S. Cl.
USPC ..... Plt./356.23

(58) Field of Classification Search
USPC ..... Plt./356.1, 356.23
See application file for complete search history.

*Primary Examiner* — Susan McCormick Ewoldt
(74) *Attorney, Agent, or Firm* — Dale Skalla

(57) ABSTRACT

A new *Petunia* plant named 'PEHY0012' particularly distinguished by fairly large size, brilliant red flowers, medium green foliage, elliptical leaves, good branching, a mounding plant habit, early flowering, and rich flowering throughout the season.

1 Drawing Sheet

Latin name of the genus and species of the plant claimed: *Petunia hybrida.*

Varietal denomination: 'PEHY0012'.

BACKGROUND OF THE NEW PLANT

The present invention comprises a new *Petunia*, botanically known as *Petunia hybrida*, and hereinafter referred to by the variety name 'PEHY0012'.

'PEHY0012' is a product of a planned breeding program. The new cultivar has fairly large size, brilliant red flowers, medium green foliage, elliptical leaves, good branching, a mounding plant habit, early flowering, and rich flowering throughout the season.

'PEHY0012' originated from a hybridization made in October 2010 in a controlled breeding environment in Enkhuizen, Netherlands.

The female parent was the unpatented proprietary plant designated 'P09-4558-1' with light red flower color, smaller flower size, and a less branching plant habit.

The male parent of 'PEHY0012' was an unpatented proprietary plant identified as 'P0193' with red flowers and less vigour compared to 'PEHY0012'.

The resulting seeds were sown in February 2011. 'PEHY0012' was selected as a single flowering plant within the progeny of the stated cross May 25, 2011 in a controlled environment in Enkhuizen, Netherlands.

The first act of asexual reproduction of 'PEHY0012' was accomplished when vegetative cuttings were propagated from the initial selection in June 2011 in a controlled environment in Enkhuizen, Netherlands

BRIEF SUMMARY OF INVENTION

Horticultural examination of plants grown from cuttings of the plant initiated in September 2001 in Angers, France, and continuing thereafter, has demonstrated that the combination of characteristics as herein disclosed for 'PEHY0012' are firmly fixed and are retained through successive generations of asexual reproduction.

'PEHY0012' has not been observed under all possible environmental conditions. The phenotype may vary significantly with variations in environment such as temperature, light intensity, and day length.

A Plant Breeder's Right for this cultivar was applied for in the European Community Plant Variety Office (CPVO) on Jun. 27, 2014, No. 2014/1720. 'PEHY0012' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawing shows typical flower and foliage characteristics of 'PEHY0012' with colors being as true as possible with an illustration of this type.

Figure 1:
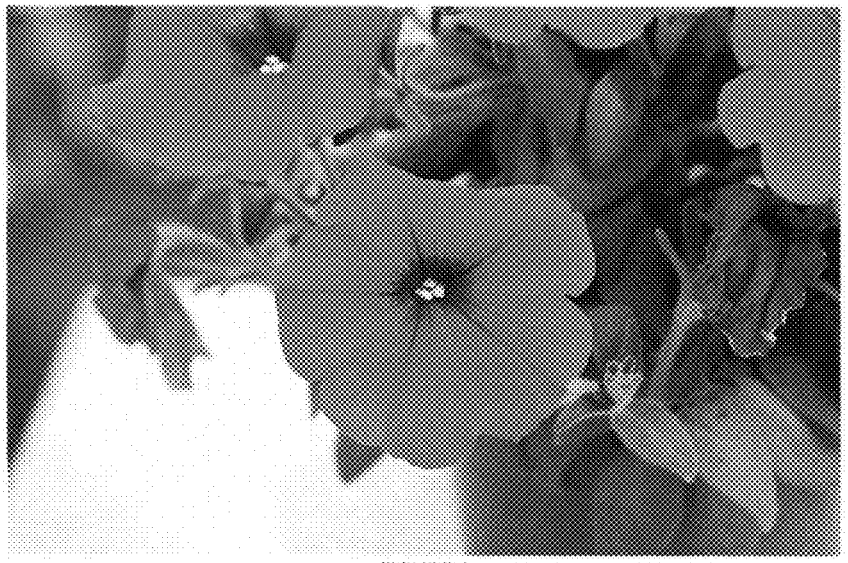
Figure 2:
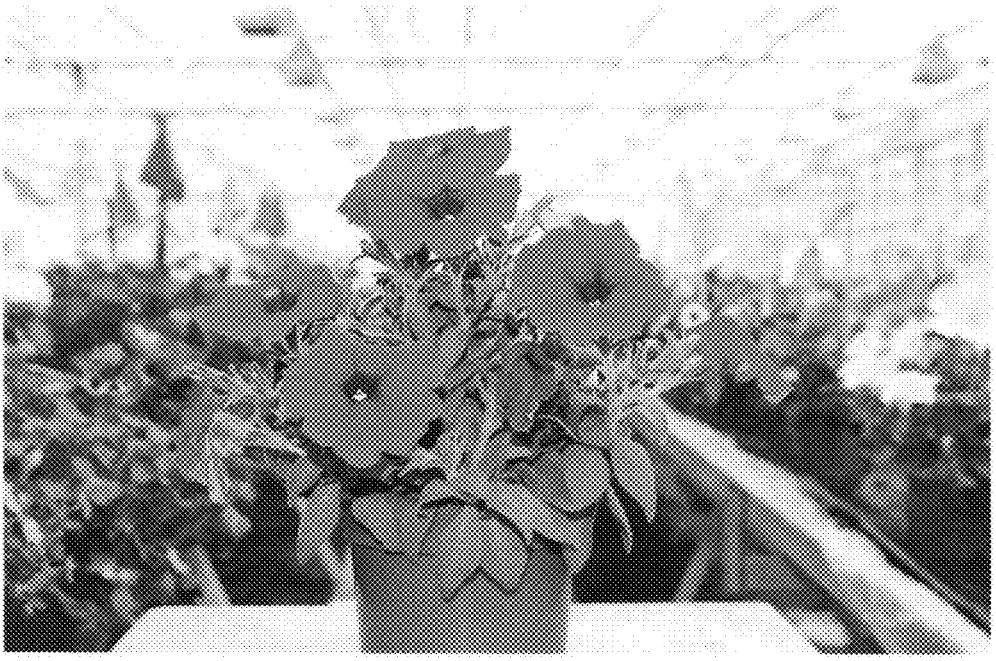

The photographic drawing shows in FIG. 1 a close-up of the flowers, and in FIG. 2 a flowering plant of the new variety.

DETAILED BOTANICAL DESCRIPTION

The plant descriptions and measurements were taken in early October 2014, from plants grown for breeding purposes in a greenhouse in Enkhuizen, Netherlands. The plants had been planted around Jul. 10, 2014. They were approximately 13 weeks of age and growing in 19 cm containers. They had been cut back a few weeks before the observations.

The aforementioned photographs were taken in April 2014 from plants growing in a greenhouse trial in Andijk, Netherlands. These plants were approximately 12-13 weeks of age.

Color references are made to The Royal Horticultural Society Colour Chart (R.H.S.) 2001.

TABLE 1

DIFFERENCES BETWEEN THE NEW VARIETY 'PEHY0012' AND A SIMILAR VARIETY

| | 'PEHY0012' | 'POTUNIA PLUS RED'('Dueplure', U.S. plant patent not found) |
|---|---|---|
| Flower color: | Red, RHS 45B, more uniform color; throat with weak pattern of dark | Main color red, RHS 45B, with almost black throat and very strong dark veins |
| Leaf, shape: | More elliptical | Ovate |
| Corolla, apex shape: | More distinct petal lobes | Petals completely fused, no lobes |

Plant:

*Form, growth and habit.*—Compact and mounding, free flowering.

*Plant height.*—14 cm.

*Plant height (inflorescence included).*—20 cm.

*Plant width.*—30 cm.

*Fragrance.*—None.

Roots:

*Number of days to initiate and produce roots.*—About 12 days at about 22 degrees C.

*Number of days to produce a liner.*—18-24 days at about 22 degrees C.

*Type.*—Fine, fibrous, free branching.

*Color.*—RHS N155B.

Foliage:

*Arrangement of leaves.*—Simple, opposite, sometimes decussate.

Immature leaf:

*Color, upper surface.*—Between RHS 143A and RHS 146B.

*Color, lower surface.*—RHS 143B and RHS 146C.

Mature leaf:

*Color, upper surface.*—RHS 146A.

*Color, lower surface.*—RHS 146B to RHS 146C.

*Length.*—6-8 cm.

*Width.*—2.8-3.2 cm.

*Shape.*—Elliptic, somewhat wavy.

*Base shape.*—Obtuse.

*Apex shape.*—Obtuse.

*Margin.*—Entire.

*Texture, upper surface.*—Hirsute.

*Texture, lower surface.*—Hirsute, shorter hair.

*Color of veins, upper surface.*—RHS 143A.

*Color of veins, lower surface.*—RHS 144A.

*Petiole, color.*—RHS 144C to RHS 144D.

*Length.*—0.7-0.8 cm.

*Diameter.*—0.5 cm.

*Texture.*—Pubescent.

Stem:

*Quantity of main branches per plant.*—5.

*Color of stem.*—RHS 144A.

*Length of stem.*—10-14 cm.

*Diameter.*—0.4 cm.

*Length of internodes.*—2 cm.

*Texture.*—Hirsute and glandular hair.

*Pedicel, color.*—RHS 144B.

*Length.*—2.5-3 cm.

*Diameter.*—0.2 cm.

*Texture.*—Hirsute, glandular hair.

Inflorescence:

*Type of inflorescence.*—Single flowers, emerging from the upper nodes of the stem.

*Blooming habit.*—Continuously through the summer months, little affected by heat.

*Quantity of flowers per plant.*—About 10-15.

*Lastingness of individual blooms on the plant.*—Up to 2 weeks, depending on temperature.

Bud (just when opening/showing color):

*Color (from the base to the top).*—Brown, RHS 199C, soon turning purple brown, RHS 182C.

*Length.*—4.5 cm.

*Width.*—1.2 cm at the top.

*Shape.*—Oblong.

Immature flower:

*Color, upper surface.*—RHS 46B.

*Color, lower surface.*—RHS 47D.

*Diameter.*—5.5-6 cm.

*Vertical length.*—4 cm.

*Aspect.*—Petals a little overhanging (re-flexed).

Mature flower:

*Shape.*—Salver-shape, with funnel-shaped base, formed by 5 fused petals.

*Flower, horizontal diameter.*—About 6.0-6.5 cm.

*Flower, vertical diameter.*—About 5 cm.

*Corolla, color upper surface.*—RHS 45B, uniform, nearly no dark veins.

*Corolla, color lower surface.*—RHS 47D.

*Apex shape.*—Truncate, hardly any distinct lobes.

*Corolla base.*—Funnel-shape.

*Margin.*—Entire.

*Waviness of margin.*—Weak to medium.

*Petal lobation.*—Weak.

*Texture, upper surface.*—Glabrous, papillose.

*Texture, lower surface.*—Papillose, hirsute, apart from the margin area.

*Corolla tube, color inner side ('throat').*—RHS 184B to RHS 184C, more yellowish towards base; with a relatively weak pattern of dark veins, RHS N187A.

*Corolla tube, color outer surface.*—RHS 199B to RHS 199C.

*Corolla tube, length.*—3.0-3.5 cm.

*Corolla tube, diameter.*—0.9 cm.

*Corolla tube, texture.*—Inner side glabrous, outer surface hirsute.

Calyx:

*Sepals, quantity.*—5 in a whorl, fused at the base.

*Color, upper surface.*—RHS 146A.

*Color, lower surface.*—RHS 146B.

*Sepal, length.*—2.3 cm.

*Sepal, width.*—0.4 cm.

*Shape.*—Ensiform.

*Apex shape.*—Acute.

*Base.*—Fused.

*Margins.*—Entire.

*Texture, upper surface.*—Hirsute, longer hairs at the edges.

*Texture, lower surface.*—Hirsute with very short hair.

Reproductive organs:

Gynoecium:

*Pistils, quantity per flower.*—1.

*Pistil length.*—2.5 cm.

*Style length.*—2.3 cm.

*Style color.*—RHS 145C.

*Stigma color.*—RHS 150D with a greener stripe, RHS 145A; and RHS 150D for the underside.

*Stigma shape.*—Round disk.

*Ovary color.*—RHS 143C.

Androecium:

*Stamens.*—5.

*Color of filaments.*—Whiter than RHS 155D.

*Length of filaments.*—2.3-2.5 cm.

*Anther color.*—Same as pollen color.

*Anther length.*—0.2-0.3 cm.

*Anther shape.*—Elliptical.

*Color of pollen.*—RHS 155A.

*Pollen amount.*—Plenty.

Fertility/seed set: Has not been observed on this plant.

Disease/pest resistance: Has not been observed on this plant.

What is claimed is:

1. A new and distinct variety of *Petunia* plant named 'PEHY0012' substantially as illustrated and described herein.

* * * * *